(12) United States Patent
Masunishi

(10) Patent No.: US 7,033,318 B2
(45) Date of Patent: Apr. 25, 2006

(54) PHOTOTHERMAL ACTUATOR AND APPARATUS COMPRISING PHOTOTHERMAL ACTUATOR

(75) Inventor: Kei Masunishi, Kanagawa (JP)

(73) Assignee: PENTAX Corporation, Tokyo (JP)

( * ) Notice: Subject to any disclaimer, the term of this patent is extended or adjusted under 35 U.S.C. 154(b) by 176 days.

(21) Appl. No.: 10/721,073

(22) Filed: Nov. 26, 2003

(65) Prior Publication Data

US 2004/0106898 A1    Jun. 3, 2004

(30) Foreign Application Priority Data

Nov. 29, 2002    (JP)    ............................ P2002-347032

(51) Int. Cl.
*A61B 1/00*    (2006.01)
*A61B /06*    (2006.01)
*G02B 6/00*    (2006.01)

(52) U.S. Cl. .......................... 600/146; 600/182; 385/13

(58) Field of Classification Search ................ 600/143, 600/182, 145–146, 150–152; 385/13, 147
See application file for complete search history.

(56) References Cited

U.S. PATENT DOCUMENTS

| 4,204,742 | A | * | 5/1980 | Johnson et al. ................ 385/23 |
| 4,976,191 | A | | 12/1990 | Suzumori et al. |
| 5,152,748 | A | * | 10/1992 | Chastagner .............. 604/95.05 |
| 5,268,082 | A | | 12/1993 | Oguro et al. |
| 5,279,559 | A | * | 1/1994 | Barr ........................ 604/95.05 |
| 5,405,337 | A | | 4/1995 | Maynard |
| 5,577,992 | A | | 11/1996 | Chiba et al. |
| 5,860,914 | A | | 1/1999 | Chiba et al. |
| 6,169,269 | B1 | | 1/2001 | Maynard |
| 6,461,337 | B1 | | 10/2002 | Minotti et al. |

FOREIGN PATENT DOCUMENTS

| JP | 1-247809 | 10/1989 |
| JP | 4-275078 | 9/1992 |
| JP | 5-253175 | 10/1993 |
| JP | 6-133923 | 5/1994 |
| JP | 8-266636 | 10/1996 |
| JP | 8-510024 | 10/1996 |
| JP | 8-299447 | 11/1996 |
| JP | 8-337760 | 12/1996 |
| JP | 9-79204 | 3/1997 |
| JP | 10-1773 | 1/1998 |
| JP | 10-24014 | 1/1998 |
| JP | 10-29190 | 2/1998 |
| JP | 11-48171 | 2/1999 |
| JP | 11216186 | 10/1999 |

(Continued)

OTHER PUBLICATIONS

English Language Abstract of JP 5-253175.

(Continued)

*Primary Examiner*—John Leubecker
*Assistant Examiner*—Philip R Smith
(74) *Attorney, Agent, or Firm*—Greenblum & Bernstein, P.L.C.

(57) ABSTRACT

A photothermal actuator comprises an optical fiber bundle, a light inputting apparatus, and a thermal receiving element. The optical fiber bundle is inserted in a tube of a catheter etc. The light inputting apparatus inputs light into the optical fiber bundle. The thermal receiving element is provided on a part of an outer surface of the optical fiber bundle. The thermal receiving element is heated by the light so that the thermal receiving element and a part of the optical fiber bundle are stretched, whereby the optical fiber bundle and the tube are bent.

33 Claims, 17 Drawing Sheets

FOREIGN PATENT DOCUMENTS

| | | |
|---|---|---|
| JP | 2000135288 | 5/2000 |
| JP | 2000189518 | 7/2000 |
| JP | 2001-70453 | 3/2001 |
| JP | 2001509231 | 7/2001 |
| JP | 2001526520 | 12/2001 |

OTHER PUBLICATIONS

English Language Abstract of JP 6-133923.
English Langage Abstract of JP 8-266636.
English Langage Abstract of JP 8-299447.
English Langage Abstract of JP 8-337760.
English Langage Abstract of JP 10-1773.
English Langage Abstract of JP 10-24014.
English Langage Abstract of JP 10-29190.
English Language Abstract of JP 11-48171.
English Language Abstract of JP 11-216186.
English Language Abstract of JP 2001-70453.
English Language Abstract of JP 2000-135288.
English Language Abstract of JP 2000-189518.

* cited by examiner

SECTIONAL VIEW ALONG LINE B-B

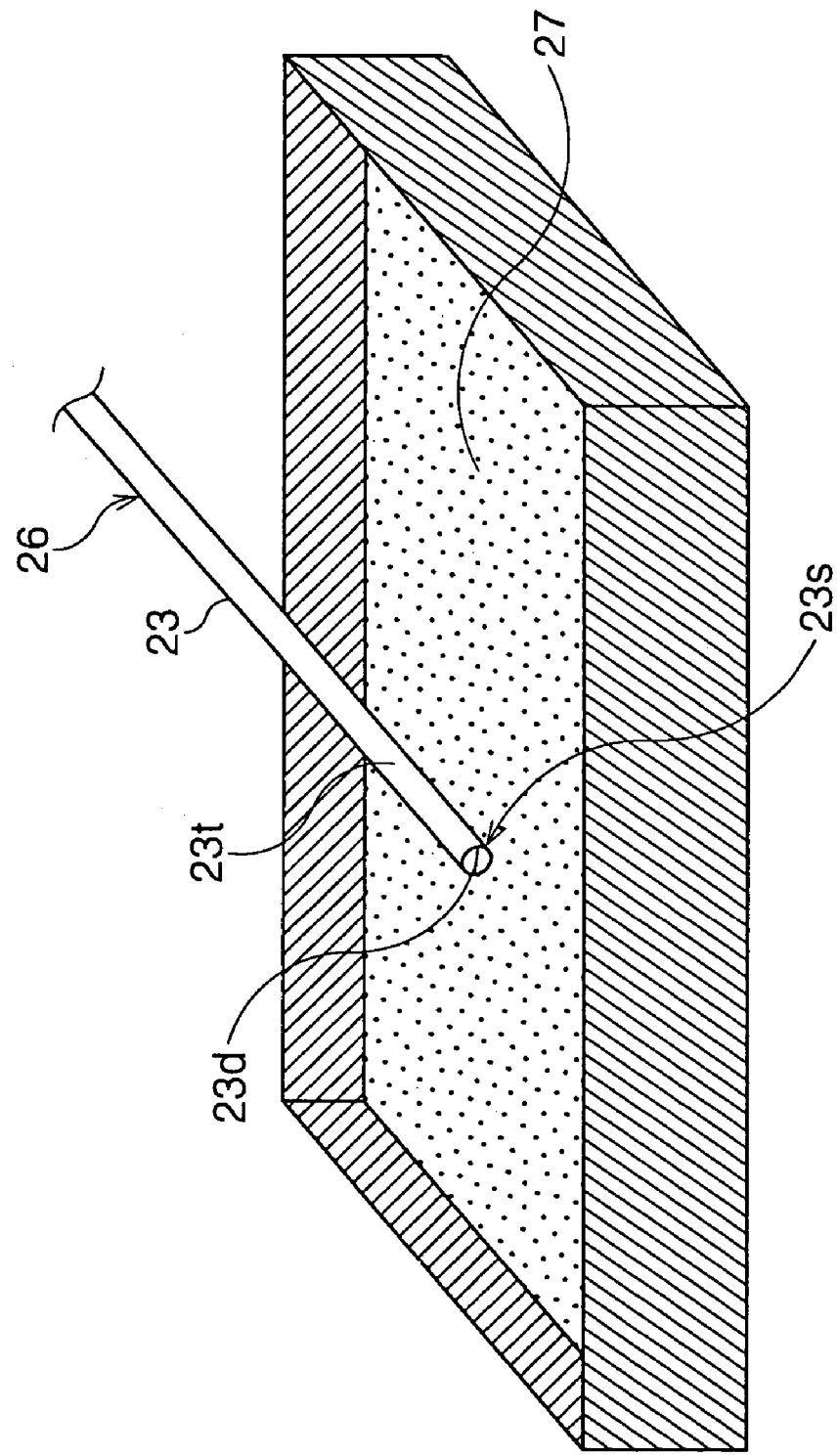

SECTIONAL VIEW
ALONG LINE A—A

SECTIONAL VIEW
ALONG LINE D–D

SECTIONAL VIEW ALONG LINE E-E

PHOTOTHERMAL ACTUATOR AND APPARATUS COMPRISING PHOTOTHERMAL ACTUATOR

BACKGROUND OF THE INVENTION

1. Field of the Invention

The present invention relates to a photothermal actuator, which is used for a guide wire, a catheter, and an endoscope etc.

2. Description of the Related Art

In the industrial field, an endoscope is used for checking or inspecting areas where a human can not enter (for example inside a gas tube) or narrow spaces which define a plurality of curved surfaces etc. In the medical field, an endoscope and a catheter are used for diagnosing and treating internal organs in order not to seriously harm the human body.

Recently, medical technology has been advancing. With these advances, diagnosis and treatment using catheters and endoscopes has been increasing. In this type of diagnosis and treatment, the catheter and the endoscope have to reach the affected area in the body through a complex path such as a meandering vein.

Therefore, conventionally the catheter and the endoscope are bent by an actuator having a shape memory alloy coil as shown in Japanese Unexamined Patent Publication (KOKAI) NO.08-299447. Further, as shown in Japanese Unexamined Patent Publication (KOKAI) NO.09-79204, conventionally the catheter and the endoscope are bent by an actuator using a fluid pressure.

However, these actuators have complex structures. Therefore, they are difficult to miniaturize. Further, when a shape memory alloy coil is used, an electric current is sent to the actuator in the human body for heating the coil of the actuator. In this situation, the electric current has to be controlled carefully. Furthermore, when using fluid pressure, the fluid pressure has to be controlled carefully too.

SUMMARY OF THE INVENTION

Therefore, an object of the present invention is to provide an actuator, which has a very simple structure, and which can be bent actively and easily. Due to this actuator, a guide wire, a catheter, and an endoscope can be bent actively and very easily.

According to the present invention, there is provided a photothermal actuator comprising an optical fiber bundle, a light inputting apparatus, and a thermal receiving element. The optical fiber bundle is inserted in a tube. The light inputting apparatus inputs light in the optical fiber bundle. The thermal receiving element is provided on a part of an outer surface of the optical fiber bundle.

The thermal receiving element is heated by light so that the thermal receiving element and a part of the optical fiber bundle are stretched, whereby the optical fiber bundle and the tube are bent. Thus, the photothermal actuator can be bent actively by using a very simple structure.

Preferably, the thermal receiving element covers half the circumference of the outer surface. Thus, the photothermal actuator can be bent in one direction effectively by using a small light volume.

If the thermal receiving element is provided on an end portion of the optical fiber bundle, the end portion can be bent. If the end portion is cut at an incline to the axis of the optical fiber bundle, the light is transformed to heat effectively.

Preferably, the thermal receiving portion is formed from at least one of a metal layer and a resin layer. Due to this, the thermal receiving portion can be produced easily.

Preferably, the optical fiber bundle is adjacent to an outer surface of the tube, and the thermal receiving portion faces the inside of the tube. Thus, it is easy for the power of the actuator to be transmitted to the tube. Preferably, the thermal receiving element covers a wedge shaped area of the end portion of the optical fiber bundle.

According to the present invention, there is provided a guide wire, a catheter, or an endoscope having the photothermal actuator described above.

According to the present invention, there is provided a guide wire, a catheter, or an endoscope having a tube and some photothermal actuators. Each photothermal actuator comprises an optical fiber bundle, and a thermal receiving element. The optical fiber bundle is inserted in the tube. Light is inputted in the optical fiber bundle by a light inputting apparatus. The thermal receiving element is provided on a part of an outer surface of the optical fiber bundle. The thermal receiving element is heated by the light so that the thermal receiving element and a part of the optical fiber bundle are stretched, whereby the optical fiber bundle and the tube are bent.

Preferably, the optical fiber bundles are arranged in a concentric circle in the tube at even intervals. Thus, the guide wire, the catheter, and the endoscope can be bent in all directions.

Preferably, the optical fiber bundles are formed into a group of optical fiber bundles, and the optical fibers bundles in the group adjoin each other. Due to this, the bending power of the photothermal actuator is strong.

Preferably, the guide wire, the catheter, or the endoscope comprises a plurality of the groups of optical fiber bundles, and the plurality of the groups are arranged in a concentric circle in the tube at even intervals.

BRIEF DESCRIPTION OF THE DRAWINGS

The objects and advantages of the present invention will be better understood from the following description, with reference to the accompanying drawings in which:

FIG. 9 is a perspective view showing a process of production of the actuator in the second embodiment;

DESCRIPTION OF THE PREFERRED EMBODIMENTS

Figure 1:
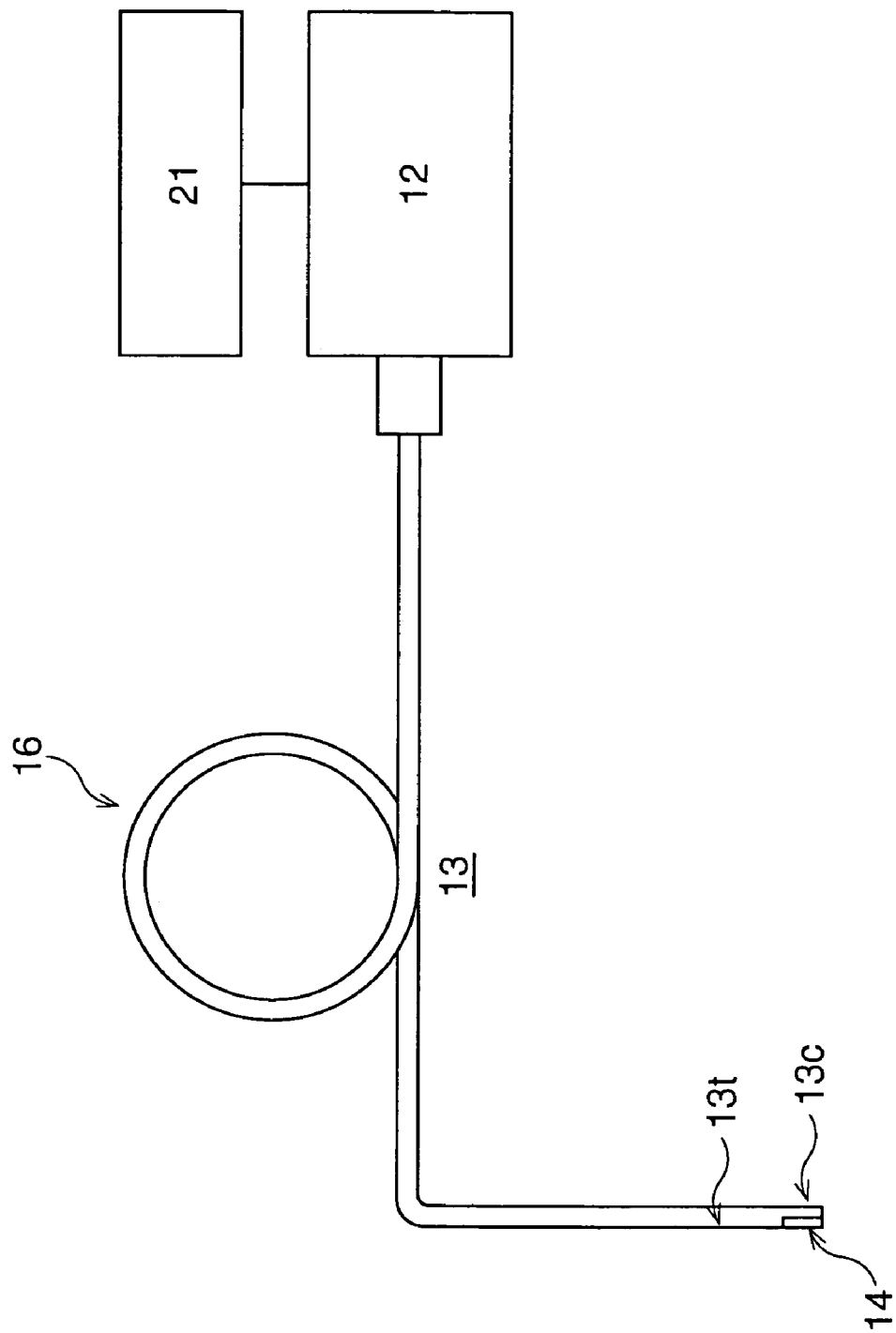
FIG. 1 is a schematic view of a basic structure of a photothermal actuator in a first embodiment.

The present invention will be described below with reference to the embodiments shown in the drawings.

FIG. 1 shows a basic structure of a photothermal actuator 16 in the first embodiment. The actuator 16 comprises an optical fiber bundle 13 and a laser light source 12 (a light inputting apparatus). The laser light source 12 inputs laser light into the optical fiber bundle 13. The inputted light is sent to an end portion 13c of the optical fiber bundle 13. The inputted light volume is controlled by a controller 21, which is connected with the laser light source 12. A thermal receiving element 14 is provided on a part of an outer surface 13t of the optical fiber bundle 13. The thermal receiving element 14 is a metal layer. A material which can be used to form the metal layer is chromium, nickel, or gold etc for example, but the material is not limited to these materials.

Figure 2:
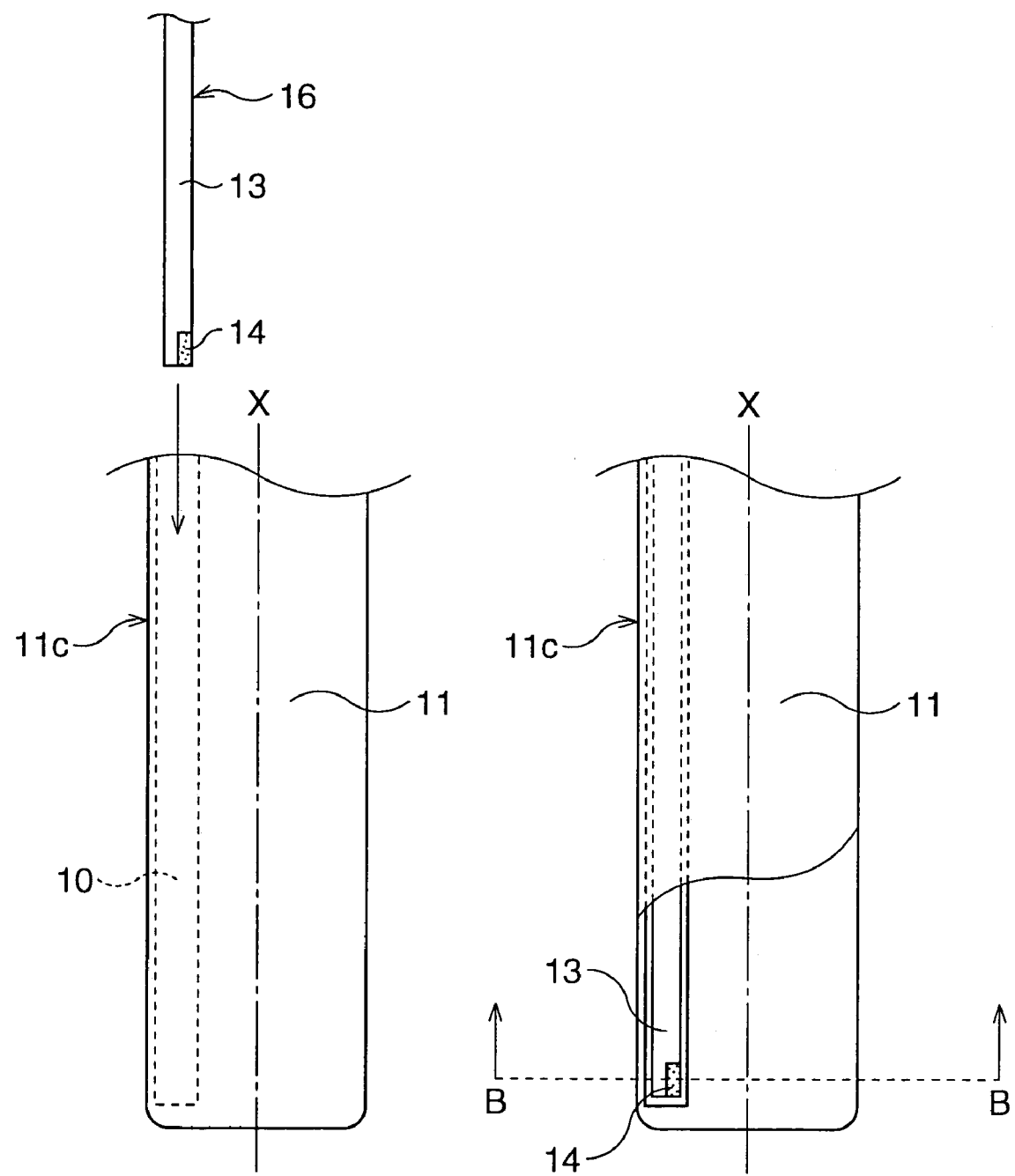
FIG. 2 is a side view of an end portion of a catheter having the actuator in the first embodiment.
Figure 3:
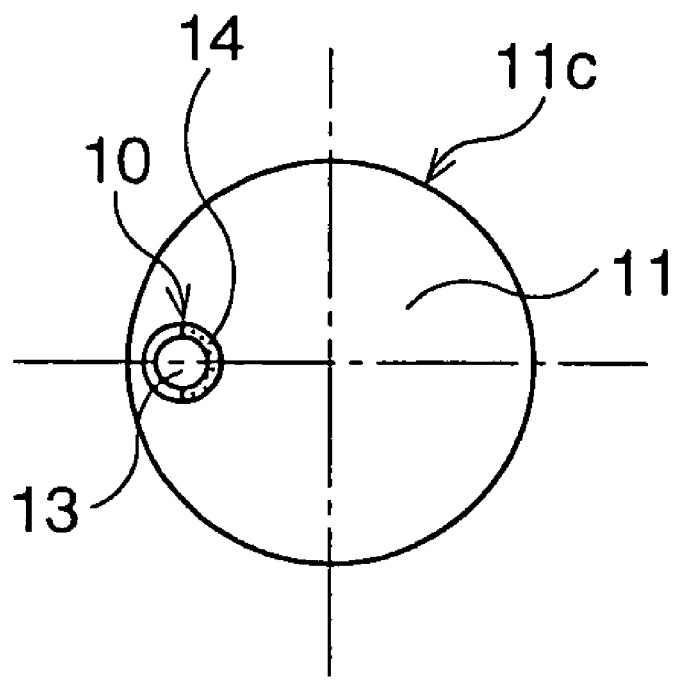
FIG. 3 is a sectional view along line B—B of FIG. 2.

FIG. 2 and FIG. 3 show an end portion of a catheter having the actuator 16 in the first embodiment. The end portion of the catheter is formed by a tube 11. The tube 11 is provided with a bundle insertion hole 10. The bundle insertion hole 10 extends in a direction parallel to an axis X of the tube 11, and is adjacent to an outer surface 11c of the tube 10. The diameter of the bundle insertion hole 10 is slightly larger than the diameter of the optical fiber bundle 13. The optical fiber bundle 13 is inserted in the bundle insertion hole 10. The thermal receiving element 14 faces the inside of tube 11, namely to the axis X of tube 11. The optical fiber bundle 13 is fixed in the tube 11 so as not to move.

Figure 4:
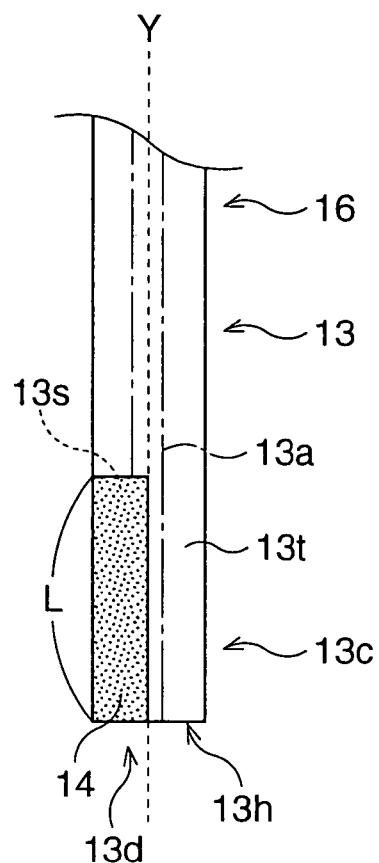
FIG. 4 is a side view of an end portion of an optical fiber bundle of the actuator in the first embodiment.
Figure 5:
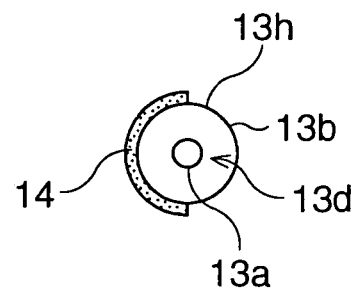
FIG. 5 is a plan view of the end portion of the optical fiber bundle in the first embodiment.

FIG. 4 and FIG. 5 show the end portion 13c of the optical fiber bundle 13 in the first embodiment. The optical fiber bundle 13 has a core portion 13a and a cladding portion 13b.

The core portion 13a is placed in the center of the optical fiber bundle 13. The cladding portion 13b surrounds the core portion 13a. The refractive index in the core portion 13a is larger than the refractive index in the cladding portion 13b. Therefore, the inputted laser light in the optical fiber bundle 13 propagates in the core portion 13a to be sent to the end portion 13c.

The end plane 13d of the optical fiber bundle 13 is perpendicular to the axis Y of the optical fiber bundle 13. The optical fiber bundle 13 is a column so the circumference 13h of the end plane 13d is a circle. The thermal receiving element 14 is curved so as to fit around half circumference of the outer surface 13t. Namely, the thermal receiving element 14 covers over a predetermined area 13s of the outer surface 13t, the predetermined area 13s extending by a predetermined length (L) from the end plane 13d. Further, the length (L) is much shorter than the length of the optical fiber bundle 13.

Figure 6:
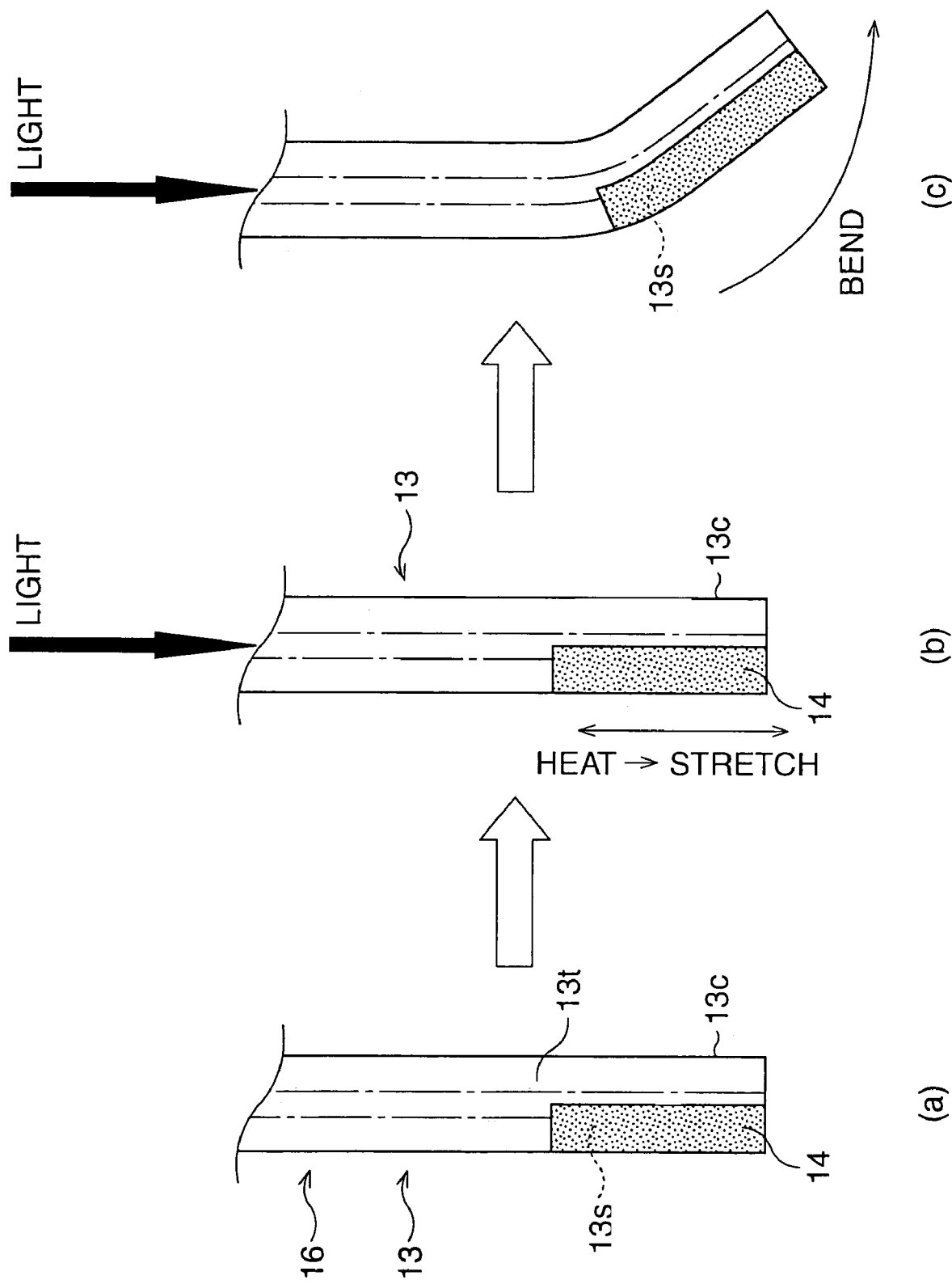
FIG. 6 is a side view showing the moving mechanism of the actuator.

FIG. 6 shows the moving mechanism of the actuator 16. As shown in FIG. 6(a), the optical fiber bundle 13 has a straight shape in the initial situation. As shown in FIG. 6(b), when the inputted light is sent to an end portion 13c of optical fiber bundle 13, the light is absorbed by the thermal receiving element 14 so that the thermal receiving element 14 is heated. Apart of this heat of the thermal receiving element 14 transmits to a part of the optical fiber bundle 13. Due to this, as shown in FIG. 6(c), the thermal receiving element 14 and one half of the circumference of the optical fiber bundle 13 are stretched, and the other half of the circumference of the optical fiber bundle 13 is not stretched. Due to this, the optical fiber bundle 13 is bent in a direction that is opposite to the area 13s where the thermal receiving element 14 covers. With the bending of the optical fiber bundle 13, the tube 11 having the bundle 13 (referred in FIG. 2) is also bent. Further, in this embodiment, the thermal receiving element 14 is formed from a metal having a coefficient of thermal expansion which is larger than that of the material of the optical fiber bundle 13, so that the bundle 13 is bent effectively.

Figure 7:
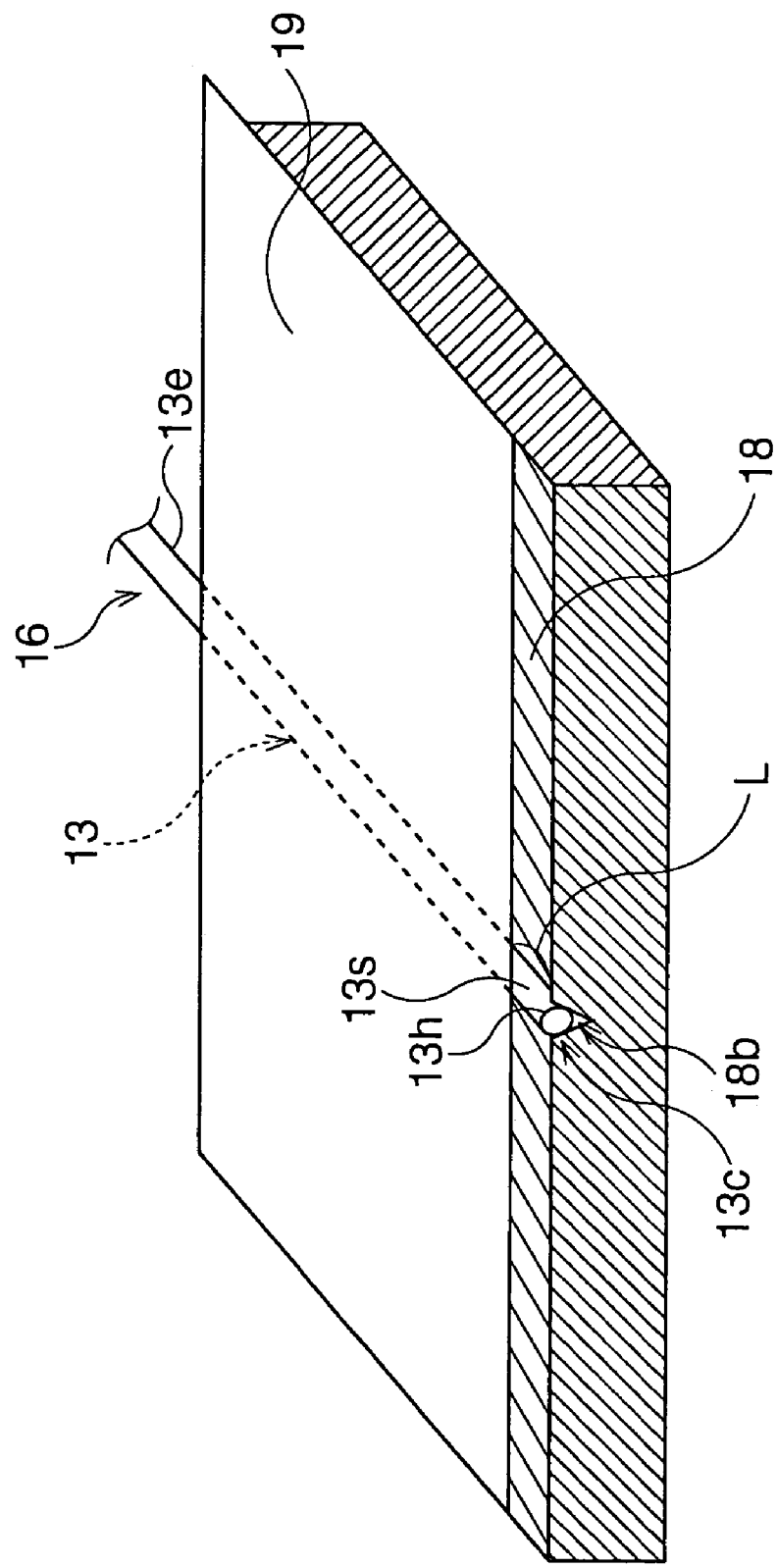
FIG. 7 is a perspective view showing a process of production of the actuator in the first embodiment.

FIG. 7 shows a process of production of the actuator 16 in the first embodiment. The process of production of the actuator 16 will be explained below. As shown in FIG. 7, first, a holder 18 having a V-shaped groove 18b is prepared. The optical fiber bundle 13 from the end portion 13c to a middle portion 13e is held in the V-shaped groove 18b. At this time, one half of the circumference of the optical fiber bundle 13 is arranged inside V-shaped groove 18b, and the other half of the circumference of the optical fiber bundle 13 projects from V-shaped groove 18b. The projecting part of the optical fiber bundle 13 is covered by a cover mask 19 between the middle portion 13e and the point, which is the length L away from the end of the bundle 13. Due to this, the predetermined area 13s whose base is half the circumference 13h and whose height is the length L, is exposed. The metal is coated on the exposed predetermined area 13s by a deposition or a sputtering process etc., so that the metal layer is formed on the predetermined area 13s.

As described above, if the thermal receiving element 14 is provided on apart of the outer surface 13t of the optical fiber bundle 13, the photothermal actuator 16 and catheter can be bent in the predetermined direction. Further, as described above, it is easy to coat the thermal receiving element 14 on the bundle 13, namely, the actuator 16 is easy to produce.

Further, the laser light which is inputted in the bundle 13 is a semiconductor laser light, a solid-state laser light, or a gas laser light etc.

Furthermore, in this embodiment, the thermal receiving element 14 is provided on the end portion 13c of the optical fiber bundle 13. However, the thermal receiving element 14 can be provided on other portions of the optical fiber bundle 13 except the end portion 13, when the optical fiber bundle 13 is bent at the other portion.

Figure 8A:
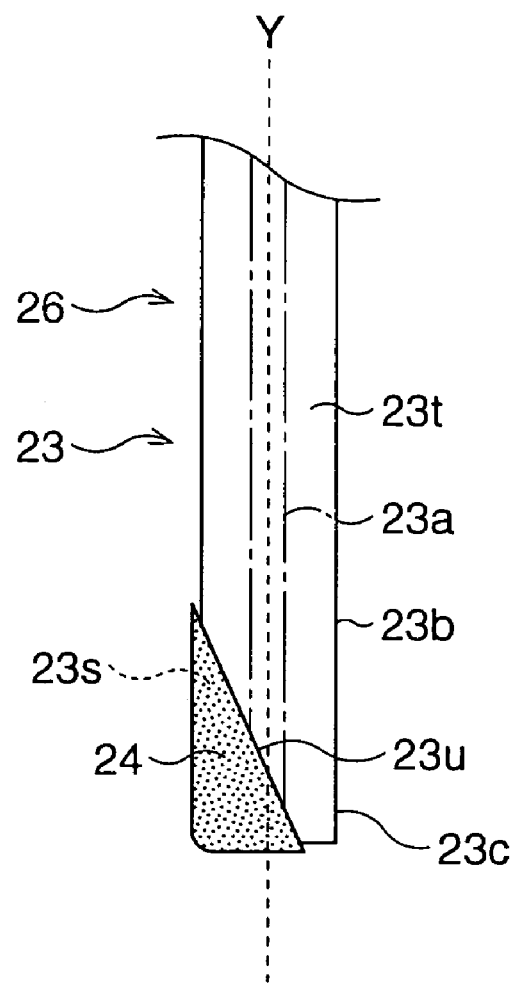
FIG. 8A is a side view of an end portion of an optical fiber bundle in the second embodiment.
Figure 8B:
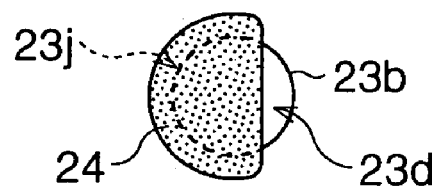
FIG. 8B is a plane view of the end portion of the optical fiber bundle in the second embodiment.

FIG. 8A and FIG. 8B show an end portion 23c of an optical fiber bundle 23 of a photothermal actuator 26 in the second embodiment. The photothermal actuator 26 in the second embodiment has the same structure as that of the first embodiment except that a thermal receiving element 24 is formed from a resin. The differences from the first embodiment will be described next.

The thermal receiving element 24 for most of the length of the thermal receiving element 24 covers approx half the circumference of an outer surface 23t. In this embodiment, specially, the thermal receiving element 24 covers over a wedge shaped area of the optical fiber bundle 23 which is defined by an oblique plane 23u to the axis Y. The oblique plane 23u passes through the end plane 23d. Namely, more than half of the end plane 23d is covered by the thermal receiving element 24 which is semicircular in the plane view, and a part of the outer surface 23t is covered by the thermal receiving element 24 which is triangular in the side view. The outside perimeter of the oblique plane 23u is a parabola.

FIG. 9 shows a process of production of the actuator 26 in the second embodiment. In this process, a synthetic resin solution 27 which is given a black color by adding a carbon black is prepared at first. The synthetic resin used for the synthetic resin solution 27 is an ultraviolet-curing resin for example. The fiber bundle 23 is immersed in the synthetic resin solution 27 at a slant to the surface of the solution 27. At this time, more than half of the end plane 23d is immersed.

Next, light is inputted in the optical fiber bundle 23 which is immersed in the solution 27 and then the light irradiates the synthetic resin solution 27. Due to this irradiation, the synthetic resin is coated around a part of the outer surface 23t and a part of the end plane 23d. Thus, the thermal receiving element 24 is formed on the optical fiber bundle 23.

Further, the thermal receiving element 24 can be formed by the process described below. First the optical fiber bundle 23 is immersed in the solution 27. Next, the bundle 23 is removed from the synthetic resin solution 27, so the synthetic resin liquid adheres to the optical fiber bundle 23. After removal, light is irradiated from outside of the optical fiber bundle 23, so the synthetic resin liquid hardens. Due to this, the thermal receiving element 24 is formed on the optical fiber bundle 23.

Further, in this process, the synthetic resin may be any other type of the resin which can be absorbed the light when it is formed on the optical fiber bundle 23. Therefore, the synthetic resin solution 27 should be given a color, and preferably the synthetic resin solution 27 is given a black color. However, it is not limited to being colored by carbon black. The synthetic resin used for the synthetic resin solution 27 is not limited to an ultraviolet-curing resin. The synthetic resin can be a liquid or a paste material which is hardened by chemical or physical action. For example, the synthetic resin can be a sensitized resin or a heat-hardening resin.

As described above, in the second embodiment, the photothermal actuator can also be bent in a predetermined direction by this simple structure.

Figure 10A:
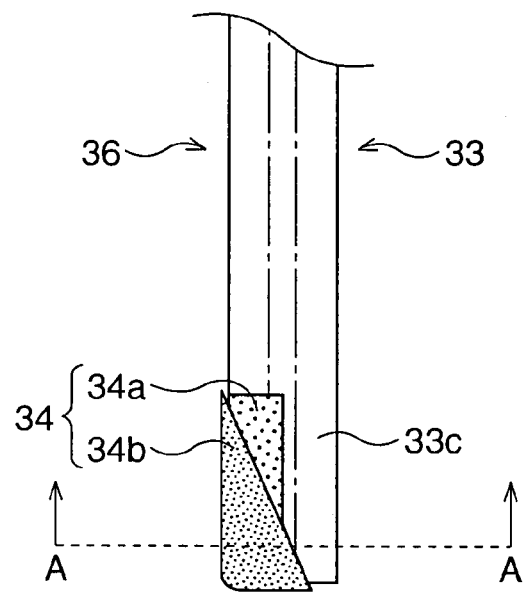
FIG. 10A is a side view of an end portion of an optical fiber bundle in the third embodiment.
Figure 10B:
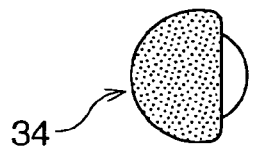
FIG. 10B is a plane view of the end portion of the optical fiber bundle in the third embodiment.
Figure 10C:
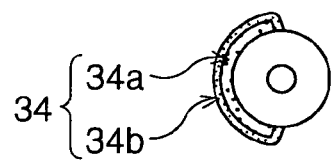
FIG. 10C is a sectional view along line A—A of FIG. 10A.

FIG. 10A, FIG. 10B, and FIG. 10C show a photothermal actuator 36 in the third embodiment. In this embodiment, a thermal receiving element 34 is formed of the metal layer in the first embodiment, and the resin layer in the second embodiment. Namely, a metal layer 34a having the same structure as the thermal receiving element 14 in the first embodiment covers the optical fiber bundle 33, and the resin layer 34b having the same structure as the thermal receiving element 24 in the second embodiment covers over the metal layer 34a. The process of production and the other structures of the photothermal actuator 36 are the same as those in the first and second embodiments. In the third embodiment, the thermal receiving element 34 transforms the light into heat more effectively than the elements in the first and second embodiments.

Figure 11A:
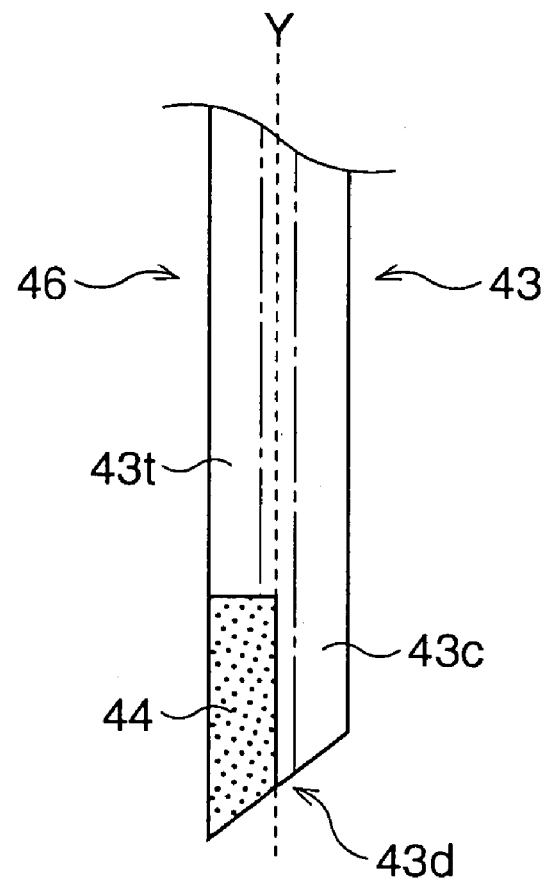
FIG. 11A is a side view of an end portion of an optical fiber bundle in the forth embodiment.
Figure 11B:
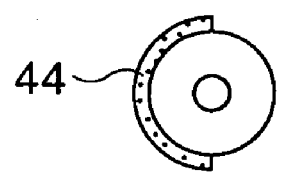
FIG. 11B is a plane view of the end portion of the optical fiber bundle in the forth embodiment.

FIG. 11A and FIG. 11B show a photothermal actuator 46 in the forth embodiment. The photothermal actuator 46 of the forth embodiment has the same structure as that of the first embodiment except that an end portion 43c of an optical fiber bundle 43 is a column cut at an incline to the axis Y of the column (the optical fiber bundle 43). Therefore, the end of optical fiber bundle 43 becomes an edge. A thermal receiving element 44 covers half the circumference of the optical fiber bundle 43 including the edge. The bending rigidity of the end portion 43c becomes small due to this structure, so that it is easier to bend the optical fiber bundle 43.

Furthermore, when an end plane 43d extends in an oblique direction to the axis at an angle of 45°, all of the inputted light in the optical fiber bundle 43 is reflected at the end plane 43d so that all of the inputted light irradiates an outer surface 43t of the bundle 43. Therefore, a thermal receiving element 44 transforms the light into heat more effectively.

As described above, the photothermal actuator can be easily bent by using a small amount of light in this embodiment.

Further, in this embodiment, the metal layer is formed in a similar way to that in the first embodiment after cutting the end portion 73c and polishing the cut surface, so that the photothermal actuator 46 is obtained.

Figure 12A:
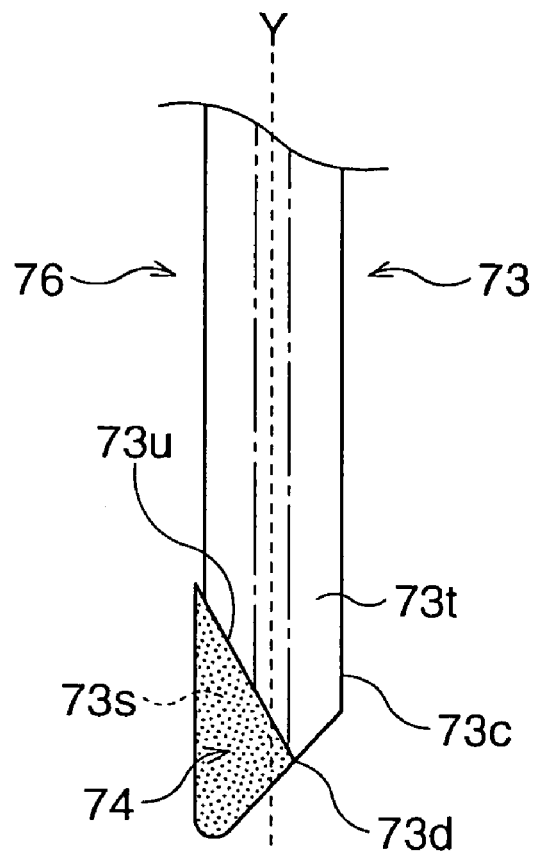
FIG. 12A is a side view of an end portion of an optical fiber bundle in the fifth embodiment.
Figure 12B:
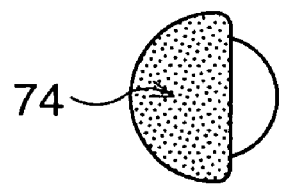
FIG. 12B is a plane view of the end portion of the optical fiber bundle in the fifth embodiment.

FIG. 12A and FIG. 12B show a photothermal actuator 76 in the fifth embodiment. The photo thermal actuator 76 in the fifth embodiment has the same structure as that of the forth embodiment except that a thermal receiving element 74 is formed from a resin. Namely, the structure of the thermal receiving element 74 is similar to that in the second embodiment.

In this embodiment, an end portion 73c of the optical fiber bundle 73 is a column cut at an incline to the axis Y of the column. Due to this, an end plane 73d is inclined. The thermal receiving element 74 covers a wedge shaped area of the optical fiber bundle 73 which is defined by an oblique plane 73u to the axis Y. The plane 73u is oblique to the end plane 73d, and passes through the end plane 73d. Namely, the end plane 73d and the outer surface 73t are covered by the thermal receiving element 74 in a similar way to that in the second embodiment.

Further, in this embodiment, the resin layer is coated in a similar way to that in the second embodiment after cutting the end portion 73c and polishing the cut surface, so that the photothermal actuator 76 is obtained.

Figure 13A:
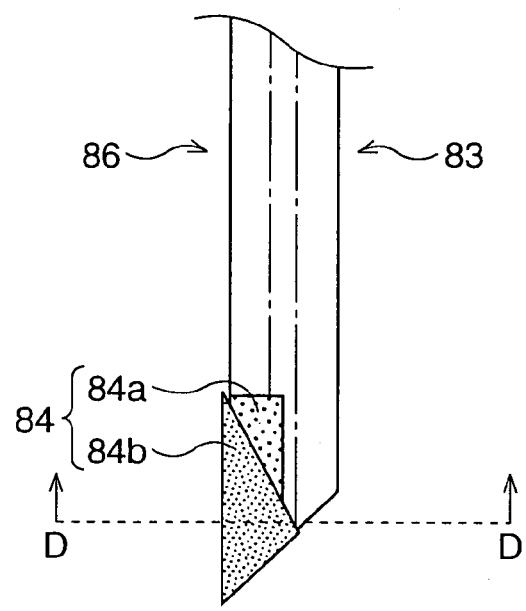
FIG. 13A is a side view of an end portion of an optical fiber bundle in the sixth embodiment.
Figure 13B:
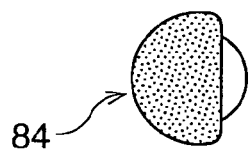
FIG. 13B is a plane view of the end portion of the optical fiber bundle in the sixth embodiment
Figure 13C:
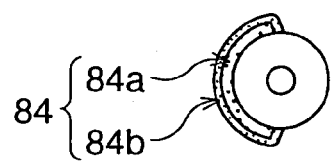
FIG. 13C is a sectional view along line D—D of FIG. 13A.

FIG. 13A, FIG. 13B, and FIG. 13C show a photothermal actuator 86 in the sixth embodiment. The photothermal actuator 86 in the sixth embodiment has the same structure as that in the forth embodiment except that a thermal receiving element 84 is formed from a metal layer 84a and a resin layer 84*b*. Namely, in this embodiment, the metal layer 84*a* having the same structure as the thermal receiving element 44 in the forth embodiment covers around an optical fiber bundle 83, and the resin layer 84*b* having the same structure as the thermal receiving element 74 in the fifth embodiment covers over the metal layer 84*a*.

Figure 14A:
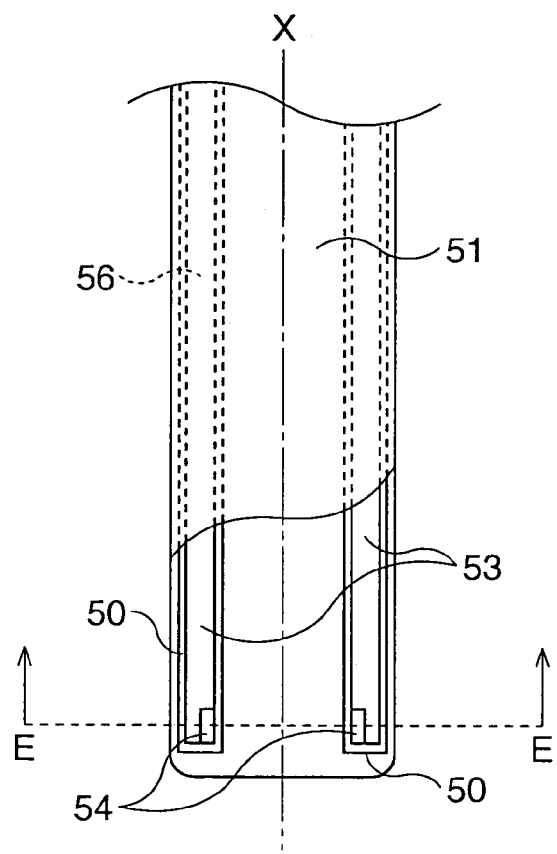
FIG. 14A is a side view of an end portion of a catheter in the seventh embodiment.
Figure 14B:
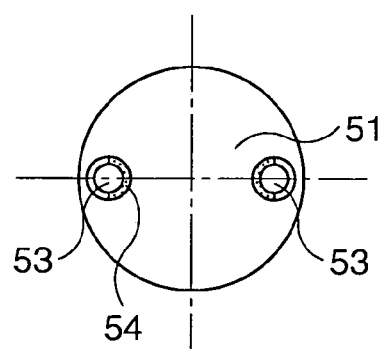
FIG. 14B is a sectional view along line E—E of FIG. 14A.

FIG. 14A and FIG. 14B show a catheter in the seventh embodiment. The catheter of the seventh embodiment has the same structure as that of the first embodiment except that two optical fiber bundles, namely two photothermal actuators are inserted in insertion holes 50 of a tube 51 of the catheter. The differences will be explained below. The tube 51 is provided with two bundle insertion holes 50.

Figure 15:
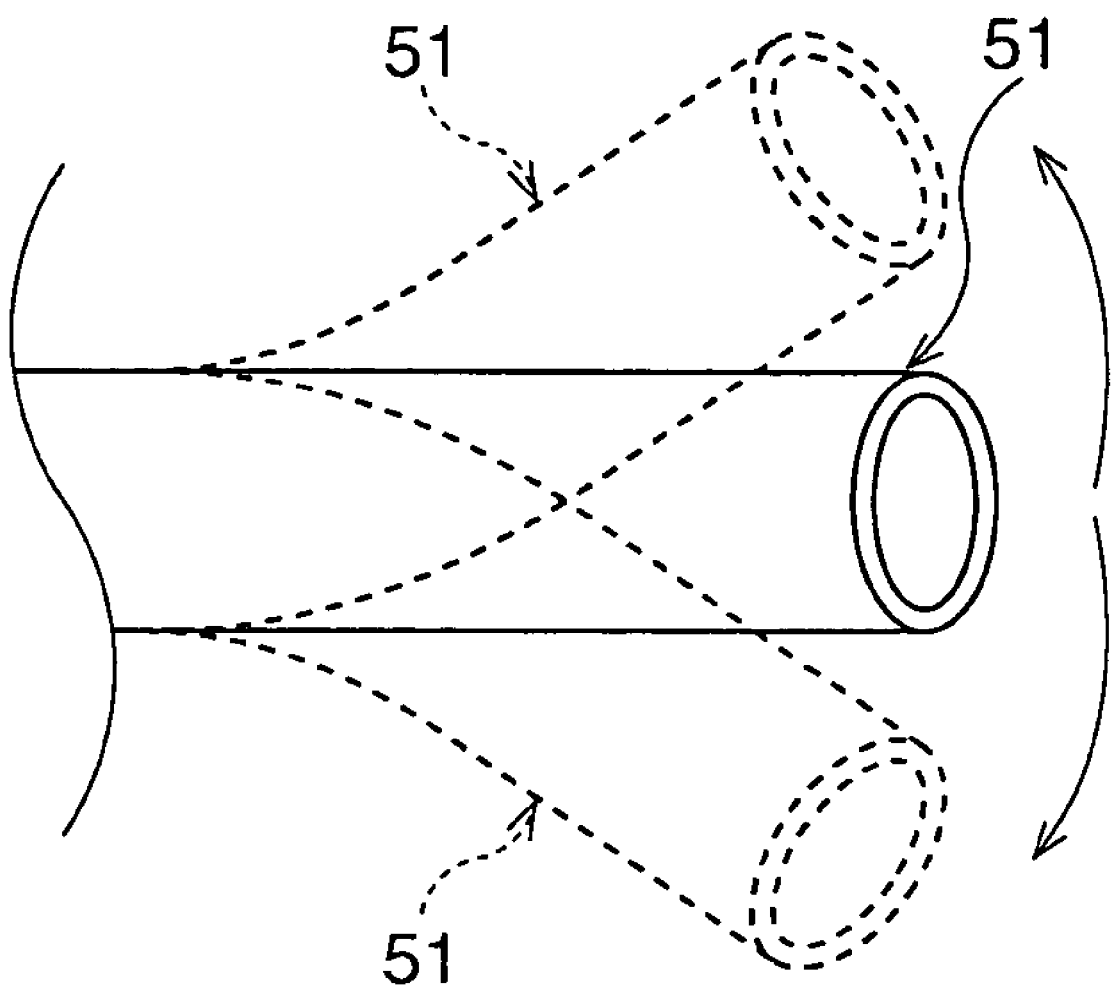
FIG. 15 is a perspective view showing a moving mechanism of a tube of the catheter in the seventh embodiment.

The two bundle insertion holes 50 are opposite each other at an angle of 180° as the axis X is a center point. The optical fiber bundles 53, namely the photothermal actuators are inserted in the insertion holes 50. The optical fiber bundles 53 have the thermal receiving element 54, which faces the inside of tube 51 as shown in FIG. 14A and FIG. 14B. Due to this, the tube 51 can be bent in two directions. Namely, as shown in FIG. 15, the direction in which the tube 51 is bent when the light is inputted in one of the optical fiber bundles 53 is opposite to the direction in which the tube 51 is bent when the light is inputted in the other of the optical fiber bundles 53.

Further, in this embodiment, the light is inputted in two optical fiber bundles 53 by using the same laser light source, which is connected with the same controller. The controller is provided with a switch. Therefore, the controller can select which optical fiber bundles the light is to be inputted, and can control the inputted light amount.

Figure 16:
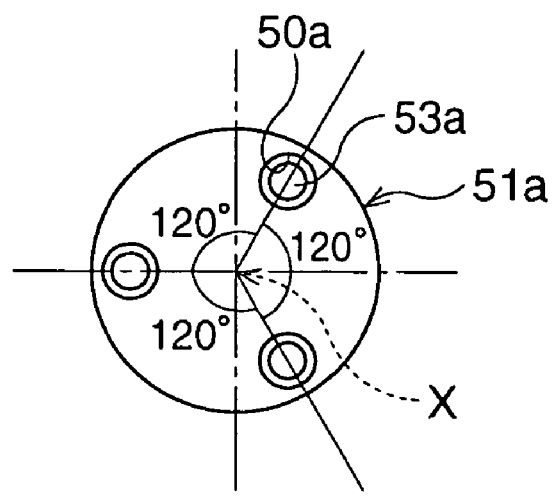
FIG. 16 is a sectional view showing an end portion of a tube of a catheter in the eighth embodiment.

FIG. 16 shows a catheter in the eighth embodiment. The catheter of the eighth embodiment has the same structure as that of the seventh embodiment except for the number of optical fiber bundles (photothermal actuators). Namely, in this embodiment, three optical fiber bundles 53*a* are inserted in insertion holes 50*a* of the tube 51*a* so as to be arranged in a concentric circle around the axis X of the tube 51*a* at even intervals, at an angle of 120°. In this embodiment, each of the inputted light amounts in the photothermal actuators 56*a* can be controlled so that the tube 51*a* can be bent in all directions, at will.

Figure 17:
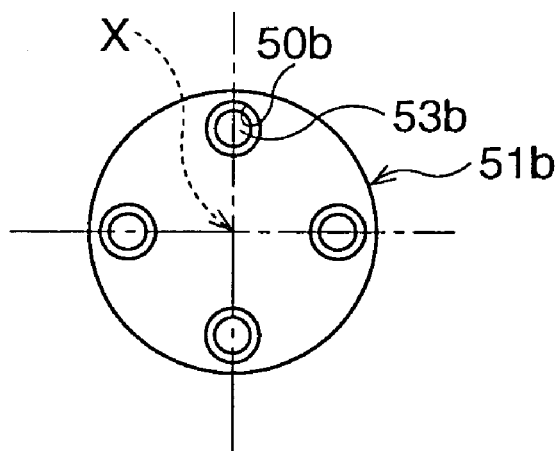
FIG. 17 is a sectional view showing an end portion of a tube of a catheter in the ninth embodiment.

FIG. 17 shows a catheter in the ninth embodiment. The catheter of the ninth embodiment has the same structure as that of the eighth embodiment except for the number of the optical fiber bundles (photothermal actuators). Namely, in this embodiment, four optical fiber bundles 53*b* are inserted in insertion holes 50*b* of the tube 51*b* to be arranged in a concentric circle around the axis X of the tube 51*b* at even intervals, at an angle of 90°.

Figure 18:
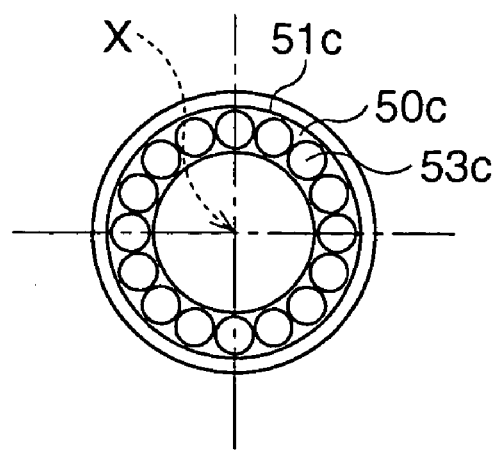
FIG. 18 is a sectional view showing an end portion of a tube of a catheter in the tenth embodiment.

FIG. 18 shows a catheter in the tenth embodiment. The catheter of the tenth embodiment has the same structure as that of the ninth embodiment except that a plurality of the optical fiber bundles (photothermal actuators) are inserted in a tube 51*c*. In this embodiment, the tube 51*c* is provided with a bundle insertion hole 50*c* which is a ring shaped column around the axis X of the tube 51*c*. The ring width is slightly larger than the diameter of the optical fiber bundle 53*c*. The plurality of optical fiber bundles 53*c* are inserted in the bundle insertion hole 50*c* in a concentric circle around the axis X of the tube 51*c*. In this embodiment, the adjoining photothermal actuators contact each other. Due to this, the tube 51*c* can be bent in all directions easily.

Figure 19:
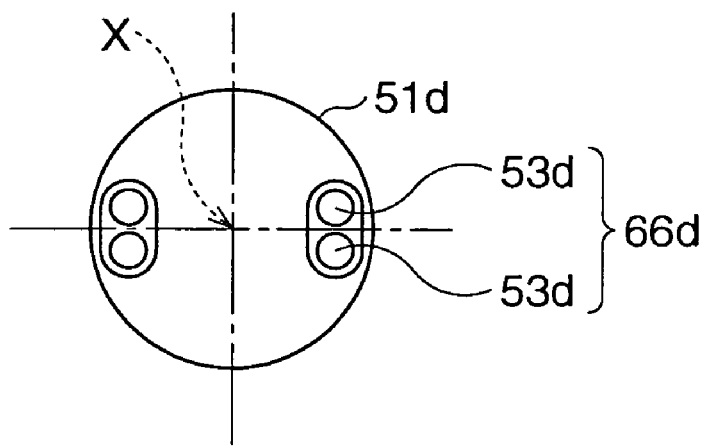
FIG. 19 is a sectional view showing an end portion of a tube of a catheter in the eleventh embodiment.

FIG. 19 shows the catheter in the eleventh embodiment. The catheter in the eleventh embodiment has the same structure as that of the seventh embodiment except two optical fiber bundles 53*d* are formed into a group 66*d*. In this embodiment, the catheter is provided with two groups 66*d* of the optical fiber bundles 53*d*. The group has two optical fiber bundles 53*d* which adjoin to contact each other. The two groups 66*d* are opposite to each other at an angle of 180° as the axis X is the center point. Due to this, the tube 51*d* can be bent in a direction with a stronger power than that in seventh embodiment. Further, each of the groups 66*d* of the optical fiber bundles can be formed by more than two optical fiber bundles 53*d*.

Figure 20:
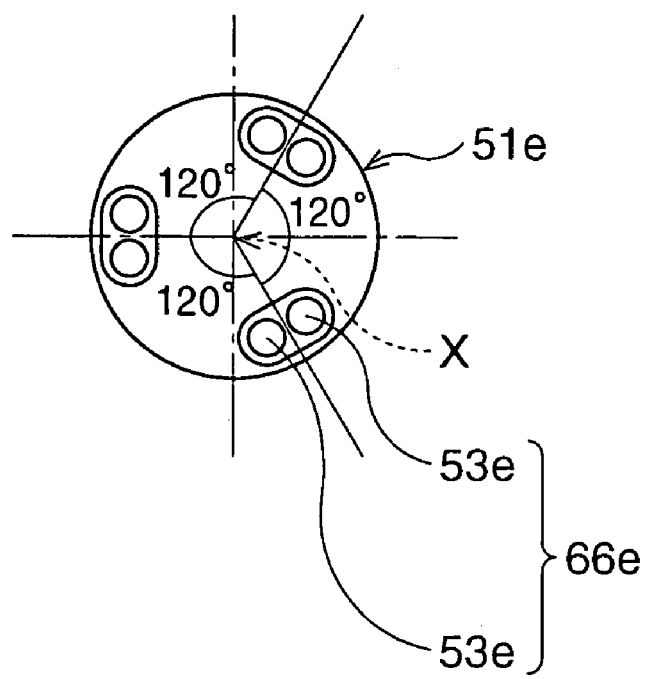
FIG. 20 is a sectional view showing an end portion of a tube of a catheter in the twelfth embodiment.

FIG. 20 shows the catheter in the twelfth embodiment. The catheter in the twelfth embodiment has the same structure as that of the eleventh embodiment except for the number of the groups of optical fiber bundles. In this embodiment, a tube 51*e* is provided with three groups 66*e* of optical fiber bundles 53*e*. Three groups 66*e* are arranged in a concentric circle around the axis X of the tube 51*b* at even intervals, at an angle of 120°. Due to this, the tube 51*e* can be bent in all directions at will, with a stronger power than that in the eighth embodiment.

Figure 21:
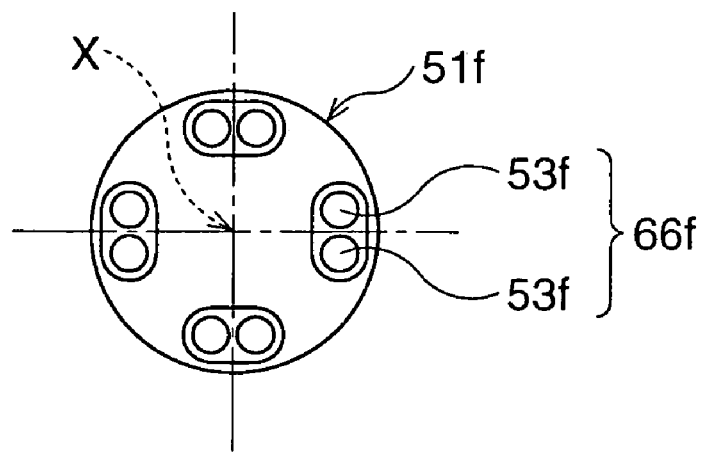
FIG. 21 is a sectional view showing an end portion of a tube of a catheter in the thirteenth embodiment.

FIG. 21 shows a catheter in the thirteenth embodiment. The catheter in the thirteenth embodiment has the same structure as that of the eleventh embodiment except for the number of the groups of optical fiber bundles. In this embodiment, four groups 66*f* of optical fiber bundles 53*f* are arranged in a concentric circle around the axis X of the tube 51*b* at even intervals, at an angle of 90°. number of the groups of optical fiber bundles. In this embodiment, four groups 66*f* of optical fiber bundles 53*f* are arranged in a concentric circle around the axis X of the tube 51*b* at even intervals, at an angle of 90°.

As described above, the photothermal actuators are provided on the catheter in embodiments 1 through 13. However, the photothermal actuators can be provided on a guide wire or an endoscope etc.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2002-347032 (filed on Nov. 29, 2002) which is expressly incorporated herein, by reference, in its entirety.

The invention claimed is:

1. A photothermal actuator comprising:

an optical fiber bundle that is inserted in a tube;

a light inputting apparatus that inputs light into said optical fiber bundle; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent;

wherein said thermal receiving element is provided on an end portion of said optical fiber bundle; and wherein said end portion is cut at an incline to the axis of said optical fiber bundle.

2. An actuator according to claim 1, wherein said thermal receiving element covers a wedge shaped area of an end portion of said optical fiber bundle.

3. A guide wire having a photothermal actuator, said photothermal actuator comprising:

an optical fiber bundle that is inserted in a tube;

a light inputting apparatus that inputs light into said optical fiber bundle; and a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

4. A guide wire having a tube and some photothermal actuators, each photothermal actuator comprising:
an optical fiber bundle in which light is inputted by a light inputting apparatus, said optical fiber bundle being inserted in said tube; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

5. A guide wire according to claim 4, wherein said optical fiber bundles are arranged in a concentric circle in said tube at even intervals.

6. A guide wire according to claim 4, wherein said optical fiber bundles are formed into a group of optical fiber bundles, said optical fibers bundles in said group adjoining each other.

7. A guide wire according to claim 6, wherein said guide wire comprises a plurality of said groups, and said groups are arranged in a concentric circle in said tube at even intervals.

8. A catheter having a photothermal actuator, said photothermal actuator comprising:
an optical fiber bundle that is inserted in a tube;
a light inputting apparatus that inputs light into said optical fiber bundle; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

9. A catheter having a tube and some photothermal actuators, each photothermal actuator comprising:
an optical fiber bundle in which light is inputted by a light inputting apparatus, said optical fiber bundle being inserted in said tube; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

10. A catheter according to claim 9, wherein said optical fiber bundles are arranged in a concentric circle in said tube at even intervals.

11. A catheter according to claim 9, wherein said optical fiber bundles are formed into a group of optical fiber bundles, said optical fibers bundles in said group adjoining each other.

12. A catheter according to claim 11, wherein said guide wire comprises a plurality of said groups, and said groups are arranged in a concentric circle in said tube at even intervals.

13. An endoscope having a photothermal actuator, said photothermal actuator comprising:
an optical fiber bundle that is inserted in a tube;
a light inputting apparatus that inputs light into said optical fiber bundle; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

14. An endoscope having a tube and some photothermal actuators, each photothermal actuator comprising:
an optical fiber bundle in which light is inputted by a light inputting apparatus, said optical fiber bundle being inserted in said tube; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent;
wherein said thermal receiving element is provided on an end portion of said optical fiber bundle; and
wherein said end portion is cut at an incline to the axis of said optical fiber bundle.

15. An endoscope according to claim 14, wherein said optical fiber bundles are arranged in a concentric circle in said tube at even intervals.

16. An endoscope according to claim 14, wherein said optical fiber bundles are formed into a group of optical fiber bundles, said optical fibers bundles in said group adjoining each other.

17. An endoscope according to claim 16, wherein said endoscope comprises a plurality of said groups, and said groups are arranged in a concentric circle in said tube at even intervals.

18. A photothermal actuator comprising:
an optical fiber bundle that is inserted in a tube;
a light inputting apparatus that inputs light into said optical fiber bundle; and
a thermal receiving element that is provided on a part of an outer surface of said optical fiber bundle,
said thermal receiving element being heated by said light so that said thermal receiving element and a part of said optical fiber bundle are stretched, whereby said optical fiber bundle and said tube are bent, and
wherein said thermal receiving element covers a wedge shaped area of an end portion of said optical fiber bundle.

19. A guide wire having a photothermal actuator, said photothermal actuator comprising:

an optical fiber bundle that is inserted in a tube;

a light inputting apparatus that inputs light into said optical fiber bundle; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

20. A guide wire having a tube and some photothermal actuators, each photothermal actuator comprising:

an optical fiber bundle in which light is inputted by a light inputting apparatus, said optical fiber bundle being inserted in said tube; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

21. A guide wire according to claim 20, wherein said optical fiber bundles are arranged in a concentric circle in said tube at even intervals.

22. A guide wire according to claim 20, wherein said optical fiber bundles are formed into a group of optical fiber bundles, said optical fibers bundles in said group adjoining each other.

23. A guide wire according to claim 22, wherein said guide wire comprises a plurality of said groups, and said groups are arranged in a concentric circle in said tube at even intervals.

24. A catheter having a photothermal actuator, said photothermal actuator comprising:

an optical fiber bundle that is inserted in a tube;

a light inputting apparatus that inputs light into said optical fiber bundle; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

25. A catheter having a tube and some photothermal actuators, each photothermal actuator comprising:

an optical fiber bundle in which light is inputted by a light inputting apparatus, said optical fiber bundle being inserted in said tube; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

26. A catheter according to claim 25, wherein said optical fiber bundles are arranged in a concentric circle in said tube at even intervals.

27. A catheter according to claim 25, wherein said optical fiber bundles are formed into a group of optical fiber bundles, said optical fibers bundles in said group adjoining each other.

28. A catheter according to claim 27, wherein said guide wire comprises a plurality of said groups, and said groups are arranged in a concentric circle in said tube at even intervals.

29. An endoscope having a photothermal actuator, said photothermal actuator comprising:

an optical fiber bundle that is inserted in a tube;

a light inputting apparatus that inputs light into said optical fiber bundle; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

30. An endoscope having a tube and some photothermal actuators, each photothermal actuator comprising:

an optical fiber bundle in which light is inputted by a light inputting apparatus, said optical fiber bundle being inserted in said tube; and a thermal receiving element that is provided on a part of an outer surface of said optical fiber bundle, said thermal receiving element being heated by said light so that said thermal receiving element and a part of said optical fiber bundle are stretched, whereby said optical fiber bundle and said tube are bent, and wherein said thermal receiving element covers a wedge shaped area of an end portion of said optical fiber bundle.

31. An endoscope according to claim 30, wherein said optical fiber bundles are arranged in a concentric circle in said tube at even intervals.

32. An endoscope according to claim 30, wherein said optical fiber bundles are formed into a group of optical fiber bundles, said optical fibers bundles in said group adjoining each other.

33. An endoscope according to claim 32, wherein said endoscope comprises a plurality of said groups, and said groups are arranged in a concentric circle in said tube at even intervals.

* * * * *